United States Patent
Klingenbeck-Regn et al.

(10) Patent No.: US 7,500,782 B2
(45) Date of Patent: Mar. 10, 2009

(54) METHOD FOR DISPLACING A SUPERIMPOSED MEASURING SURFACE ON A SENSOR SURFACE OF AN X-RAY DETECTOR AND X-RAY SYSTEM FOR IMPLEMENTING SAID METHOD

(75) Inventors: Klaus Klingenbeck-Regn, Nürnberg (DE); Judith Regn, Nürnberg (DE)

(73) Assignee: Siemens Aktiengellschaft, Munich (DE)

( * ) Notice: Subject to any disclaimer, the term of this patent is extended or adjusted under 35 U.S.C. 154(b) by 0 days.

(21) Appl. No.: 11/881,717

(22) Filed: Jul. 27, 2007

(65) Prior Publication Data
US 2008/0031421 A1    Feb. 7, 2008

(30) Foreign Application Priority Data
Aug. 3, 2006    (DE) .................. 10 2006 036 272

(51) Int. Cl.
*H05G 1/02*    (2006.01)
*A61B 6/00*    (2006.01)

(52) U.S. Cl. ................... 378/197; 378/24; 378/196

(58) Field of Classification Search ............ 378/11, 378/21–26, 41, 62, 146, 196–198, 205
See application file for complete search history.

(56) References Cited

U.S. PATENT DOCUMENTS 6,208,710 B1    3/2001    Nagai
6,869,217 B2    3/2005    Rasche et al.
2003/0058996 A1    3/2003    Graumann et al.
2004/0170255 A1*    9/2004    Akutsu et al. ............... 378/197
2005/0169432 A1    8/2005    Groh et al.

FOREIGN PATENT DOCUMENTS

DE    19958864 A1    6/2001
DE    10147160 C1    4/2003
DE    102004004630 A1    8/2005

* cited by examiner

*Primary Examiner*—Edward J Glick
*Assistant Examiner*—Mona M Sanei

(57) ABSTRACT

To avoid manual adjustments, the invention relates to a method for displacing a superimposed measuring surface on a sensor surface of an x-ray detector in an x-ray system, with an x-ray source and the x-ray detector forming a recording system and being at a fixed distance from one another, with the recording system being moveable in a three-dimensional manner relative to an object to be examined, comprising: the superimposed measuring surface is displaced on the sensor surface of the x-ray detector by a first distance in a first direction; and the recording system is moved by a second distance in parallel with the first distance in a second direction, which is opposite to the first direction, whereby after implementing one of the two steps, the other step is respectively automatically implemented such that a previously superimposed examination area of the object remains superimposed on the displaced measuring surface.

20 Claims, 4 Drawing Sheets

METHOD FOR DISPLACING A SUPERIMPOSED MEASURING SURFACE ON A SENSOR SURFACE OF AN X-RAY DETECTOR AND X-RAY SYSTEM FOR IMPLEMENTING SAID METHOD

CROSS REFERENCE TO RELATED APPLICATIONS

This application claims priority of German application No. 10 2006 036 272.1 filed Aug. 3, 2006, which is incorporated by reference herein in its entirety.

FIELD OF THE INVENTION

The invention relates to a method for displacing a superimposed measuring surface on a sensor surface of an x-ray detector and an x-ray system.

BACKGROUND OF THE INVENTION

In different fields of x-ray diagnostics, fluoroscopy systems featuring different x-ray detector dimensions are generally used nowadays. A flat panel detector with an edge length of approximately 20 cm×20 cm is used within the field of cardiology and a flat panel detector with an edge length of approximately 30 cm×40 cm is used within the field of radiology for instance. The main reason for this consists in the need to find a suitable compromise between covering the organ of interest and the required angulations, e.g. of a C-arm, according to the application, since a small x-ray detector enables collisions to be more easily avoided and enables correspondingly higher angulations to be carried out, but it is nevertheless impossible for the whole heart, including the coronary vessels, to be mapped for instance.

With the increasing spread of (cardio) vascular centers, it was important, even with the exceptional use of large x-ray detectors (e.g. 42 cm×42 cm edge length) to achieve flexible configurations with extended angulation possibilities in C-arm x-ray devices for instance. In the case of a small measuring field which only requires a part of the sensor surface of the x-ray detector, one possibility consists here in eccentrically superimposing the small measuring field on the large x-ray detector. The so-called eccentric collimation enables collisions to be avoided and accordingly a higher angulation.

If a measuring field on the sensor surface of the x-ray detector is however displaced in a translatory fashion from a center position into an eccentric position, a different examination area is superimposed on the eccentrically positioned measuring field than on the center positioned measuring field. If the superimposed examination area is to remain the same however, the user must manually move the examination table, on which the object with the examination area is located, since the isocenter, which generally coincides with the center point of the examination area, of the C-arm is fixed.

SUMMARY OF THE INVENTION

The object of the present invention is to provide a method, which, in the case of an x-ray system of this type, enables a simple and cost-effective displacement of a superimposed measuring surface on a sensor surface of an x-ray detector with a constant examination area and without any manual adjustment; in particular a displacement of this type is also to be possible with an x-ray system, which records two-dimensional projections of the examination area from different perspectives in rapid sequence. Furthermore, the object of the invention is to provide an x-ray system which is suited to implementing the method.

The object is achieved in accordance with the invention by a method for displacing a superimposed measuring surface on a sensor surface of an x-ray detector and by an x-ray system as claimed in the claims. Advantageous embodiments of the invention are the subject matter of the associated subclaims in each instance.

With the method according to the invention, the mobility of a recording system, consisting of an x-ray source and the x-ray detector at a fixed distance from one another, is used relative to the object in order to provide an automatic adjustment of the recording system, so that a previously superimposed examination area of the object remains superimposed on the displaced measuring surface.

The method according to the invention has two main steps, whereby when one of the two steps is implemented in each instance, the other step follows automatically.

If, as a first step, the superimposed measuring surface on the sensor surface of the x-ray detector is displaced by a first distance in one direction, it automatically follows that the recording system is moved by a second distance parallel to the first distance in a second direction, said second direction being opposite to the first direction. The same examination area can herewith be superimposed in a center or eccentrically positioned fashion depending on requirements, in a simple manner and without having to carry out costly and time-intensive manual readjustments to the position of the object. An eccentric collimation, which offers extended angulation possibilities, can be used particularly effectively. In addition, the method according to the invention enables a rapid, dynamic sequence of different positions of the measuring surface, in real-time for instance, with the examination region remaining the same.

If, as a first step, the recording system is moved by a second distance in a second direction, it automatically follows that the superimposed measuring surface on the sensor surface of the x-ray detector is displaced by a first distance parallel to the second distance in a first direction, said first direction being opposite to the second direction. This makes it possible for a doctor to move the recording system without any difficulty for improved accessibility to the object under examination without having to subsequently carry out a costly and time-intensive manual readjustment of the position of the object. A rapid, dynamic sequence of movements, in real time for instance, is also possible with the examination area remaining the same.

The displacements and movements are generally translatory displacements and movements. The measuring area essentially remains identical in size after the displacement.

The x-ray system according to the invention contains, in addition to the moveable recording system having a x-ray detector and a x-ray source at a fixed distance from one another, a diaphragm system for forming a sub x-ray beam as well as a control unit, by means of which the movement of the recording system and the displacement of a superimposed measuring surface on the sensor surface can be controlled.

According to one embodiment of the invention, the recording system is supported by a bracket, in particular a C-arm, on which the x-ray source is arranged on one end and the x-ray detector on the other end. The bracket, in particular the C-arm, forms a simple mechanical coupling between the x-ray source and the x-ray detector at a fixed distance relative to one another.

Advantageously, the bracket can be rotated about an isocenter between the focus of the x-ray source and the x-ray detector. X-ray systems of this type are suited to recording x-ray projections from different directions, which can be reconstructed to form 3D x-ray images.

According to a further embodiment of the invention, the bracket is arranged on a robot arm, in particular an industrial robot and can be moved in a three-dimensional fashion. Robot arms and particularly industrial robots allow movements of up to six degrees of freedom.

According to one embodiment of the invention, the measuring surface on the sensor surface is displaced by adjusting a diaphragm system to form a sub x-ray beam from the x-rays. In the initial state, in other words when the measuring surface has not be moved, an original sub x-ray beam from the x-rays is superimposed by means of the diaphragm system. The generally known adjustment of the diaphragms of the diaphragm system allows a further sub x-ray beam which differs from the original sub x-ray beam to be formed from the x-rays, by means of which sub x-ray beam the measuring surface displaced into its target position is superimposed. Another possibility for displacing the measuring surface on the sensor surface can be achieved by tilting the x-ray source about its focus, an adjustment of the diaphragm is however also generally required here.

According to a further embodiment of the invention, the superimposed measuring surface is displaced from a central position into an eccentric position on the sensor surface. This corresponds to the so-called eccentric collimation of small measuring surfaces on an x-ray detector with a large sensor surface.

The second distance is advantageously determined before the recording system is moved and/or the first distance is determined before the measuring surface on the sensor surface is displaced. To determine the first and/or second distance, the second and/or the first distance as well as the distance of the focus of the x-ray source from the x-ray detector and the distance of the focus of the x-ray source from the center point of the examination area are used in each instance. The first and/or second distance can be automatically calculated or retrieved from a table. With a high-frequency sequence of displacements or movements, the respective distances and geometric ratios are also continuously recalculated.

According to a further embodiment of the invention, the examination area and the target position of the displaced measuring surface are determined and can, in particular, be selected by an operator. This can be triggered for instance by input into a user interface or by pressing different control elements provided herefor.

BRIEF DESCRIPTION OF THE DRAWINGS

The invention as well as further advantageous embodiments according to the features of the subclaims are explained in more detail below with reference to schematically illustrated exemplary embodiments, without herewith restricting the invention to said exemplary embodiments, in which;

DETAILED DESCRIPTION OF THE INVENTION

Figure 1:
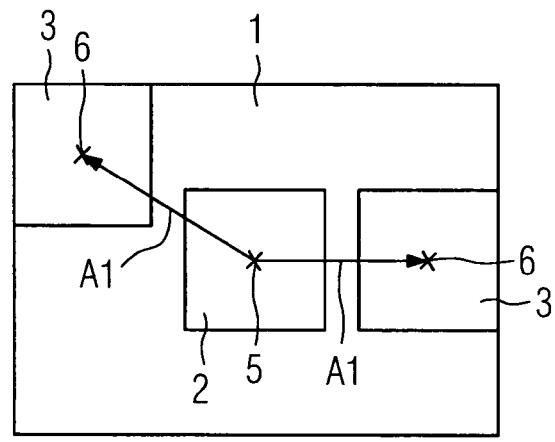
FIG. 1 shows an overhead view onto a sensor surface having one center and two eccentrically positioned measuring surfaces.

FIG. 1 shows a schematic overhead view onto a sensor surface 1 of a flat x-ray detector. X-ray detectors of this type, for instance flat panel detectors, feature an active matrix made out of a plurality of pixel readout units and a converter layer arranged upstream herefrom. In the converter layer, which can be a scintillator layer for instance, x-rays are directly converted into an electric charge or indirectly into light, in the active matrix, the electric charge is stored or the light is converted into electric charge and is then stored. The electric charge is then read out and can then be forwarded for further processing to an image system.

The sensor surface 1, which is composed of a plurality of pixel readout units, can either be switched so that it is completely sensitive to incident x-rays, or only subsurfaces which are smaller than the sensor surface but comprise at least one pixel readout unit, can be switched so as to be sensitive to incident x-rays, in order to record only small examination areas for instance. To prevent the patient from being subject to any unnecessary radiation doses, the x-rays are generally already formed by a diaphragm system such that the sub x-ray beam only radiates the corresponding sub surfaces.

FIG. 1 shows a center positioned measuring surface 2, which only fills a part of the sensor surface 1 and is arranged centrally on the sensor surface. The center point 5 of the center positioned measuring surface 2 is identical to the center point of the sensor surface 1. With some applications it is useful to superimpose small examination areas on eccentrically positioned measuring surfaces 3 on the sensor surface 1, particularly to facilitate angulations. To this end, the center positioned measuring surface 2 is displaced by a first distance A1 on the sensor surface, resulting in an eccentrically positioned measuring surface 3 with an eccentrically positioned center point 6.

Figure 2:
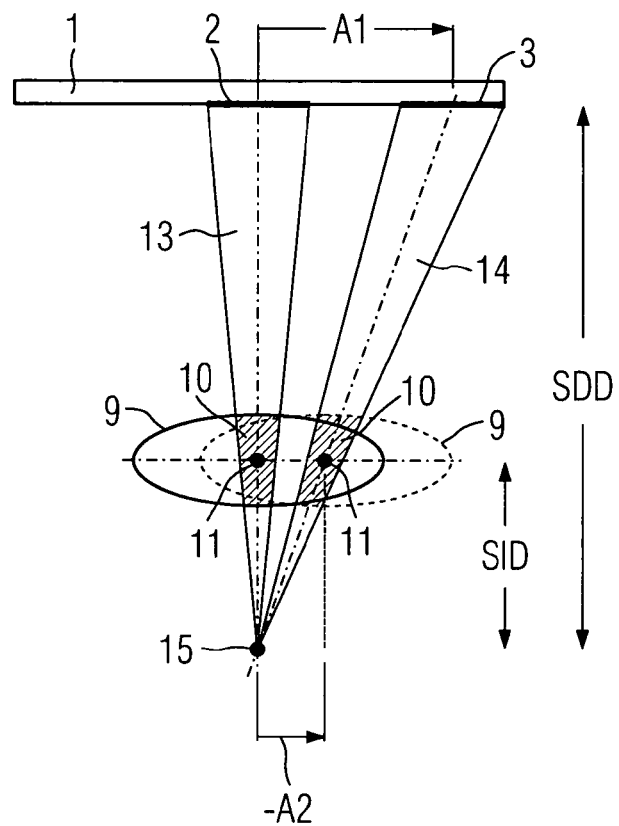
FIG. 2 shows an illustration of the geometric ratios between the focus of the x-ray source, the x-ray detector, the object and its examination area for centrally or eccentrically positioned measuring surfaces.

FIG. 2 shows the geometric relationships for a displacement of this type. A center sub x-ray beam 13 formed in general by the beam formation emanates from a focus 15 of the x-ray source and maps an examination area 10 (solid line) of an object 9 on the center positioned measuring surface 2. The examination area 10 comprises a center point 11 of the examination area 10.

The same examination area 10 is now to be mapped on the eccentrically positioned measuring area 3. To this end, the center positioned measuring surface 2 is displaced on the one hand by the first distance A1 on the eccentrically positioned measuring surface 3, by forming an eccentric sub x-ray beam 14 by means of beam formation for instance. To actually superimpose the same examination area 10 however, the examination object 9 must on the other hand, as in the prior art, either be moved parallel to the first distance and in the same direction or, according to the invention, the recording system, in other words the x-ray source and x-ray detector coupled at a fixed distance relative to one another, are moved parallel to the first distance in the opposite direction by a second distance A2. The resulting relative position of the examination area 10 and/or object 9 relative to the recording system after the movement by the second distance A2 is indicated by a dashed line.

If one of the two distances is known, either of the first distance A1 or the second distance A2, the respective other distance can be easily calculated from the distance SID between the focus and the center point of the examination area and the distance SDD between the focus and the x-ray detector. The associated formula is as follows:

$$A_1 = \frac{SID}{SDD} \cdot A_2$$

The distance of the focus of the x-ray source from the x-ray detector and the distance of the focus of the x-ray source from the center point of the examination area and/or the isocenter can now be provided or measured by the x-ray system.

Figure 3:
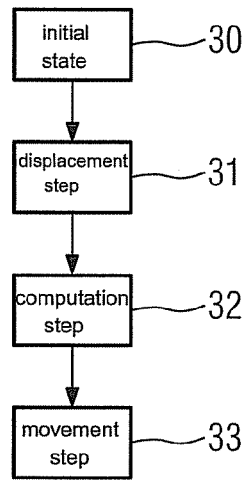
FIG. 3 shows a flow diagram of a method according to the invention.
Figure 4:
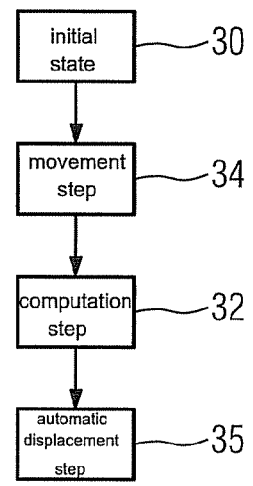
FIG. 4 shows a flow diagram of a further method according to the invention.

FIG. 3 and FIG. 4 show two alternative embodiments of an inventive method. The two alternatives differ in respect of the sequence of the two main steps: In FIG. 3 the measuring surface is displaced first and in FIG. 4 the recording system is moved first. In both cases, an initial state 30 is assumed, in which the examination area is superimposed onto a center positioned measuring surface 2. The method can also be applied to the opposite case such that the initial state is an eccentrically positioned measuring surface 3, which is to be moved onto a center positioned measuring surface 2.

From the initial state, as shown in FIG. 3, a displacement 31 of the measuring surface from a center positioned measuring surface 2 to an eccentrically positioned measuring surface 3 is carried out by a first distance A1, for instance by a user entering the target position of the measuring surface into the corresponding x-ray system by way of the user interface or by pressing a button and a diaphragm system subsequently forming x-rays such that an eccentric x-ray beam hits the eccentrically positioned measuring surface.

In a computation step 32, the second distance A2 is then calculated from the first distance A1 by a control unit for example or is retrieved from stored values. The recording system is then automatically moved in a movement step 33 by the second distance in parallel to the first distance A1 and in the opposite direction such that the examination area superimposed in the initial state is now eccentrically superimposed. Prior to the automatic movement, the x-ray system is still able to issue a confirmation request to the user.

FIG. 4 shows that the recording system is moved in a movement step 34, starting from the initial state 30, by a user entering the second distance A2 into the corresponding x-ray system by means of a user interface for instance and by the recording system being moved by the second distance A2. A movement of this type can be implemented for instance for the reason that a user requires better accessibility to a patient. In computation step 32, the first distance A1 is then calculated from the second distance A2 by the control unit or a computing unit contained therein or is retrieved from stored values.

An automatic displacement 35 of the measuring surface from a center positioned measuring surface 2 onto an eccentrically positioned measuring surface 3 on the sensor surface is then carried out by a first distance A1. The diaphragm system can in turn form the x-rays such that the eccentric x-rays hit the eccentrically positioned measuring surface. This can be applied to the diaphragm system by the control unit. Provision can also be made for a confirmation request to be issued to the user and for a warning to be issued if it is determined by the control unit or the computing unit for instance that the eccentrically positioned measuring surface is migrating beyond the edge of the sensor surface.

In both cases described in FIG. 3 and FIG. 4, a dynamic adjustment of the respective second step, in other words a real-time adjustment, is possible, since a continuous calculation or querying of the first or second distance from the second or first distance and the remaining two distances can be carried out very rapidly. The real-time adjustment is expedient in x-ray systems for instance, in which the recording system is continuously moved by an industrial robot and thus a likewise continuous displacement of the measuring surface on the sensor surface is necessary. In this case, the edges of the diaphragm jaws in the x-ray image can alternatively be continuously redetected using fluoroscopy, thereby determining and accordingly automatically adjusting the geometrical modifications.

Figure 5:
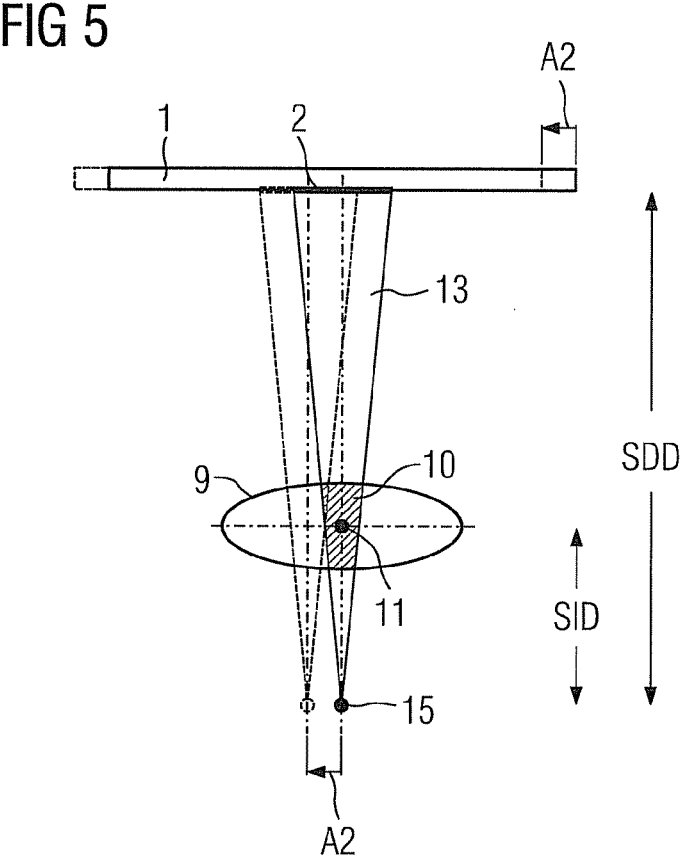
FIG. 5 shows an illustration of the geometric ratios with an inventive method as claimed in to FIG. 4.
Figure 6:
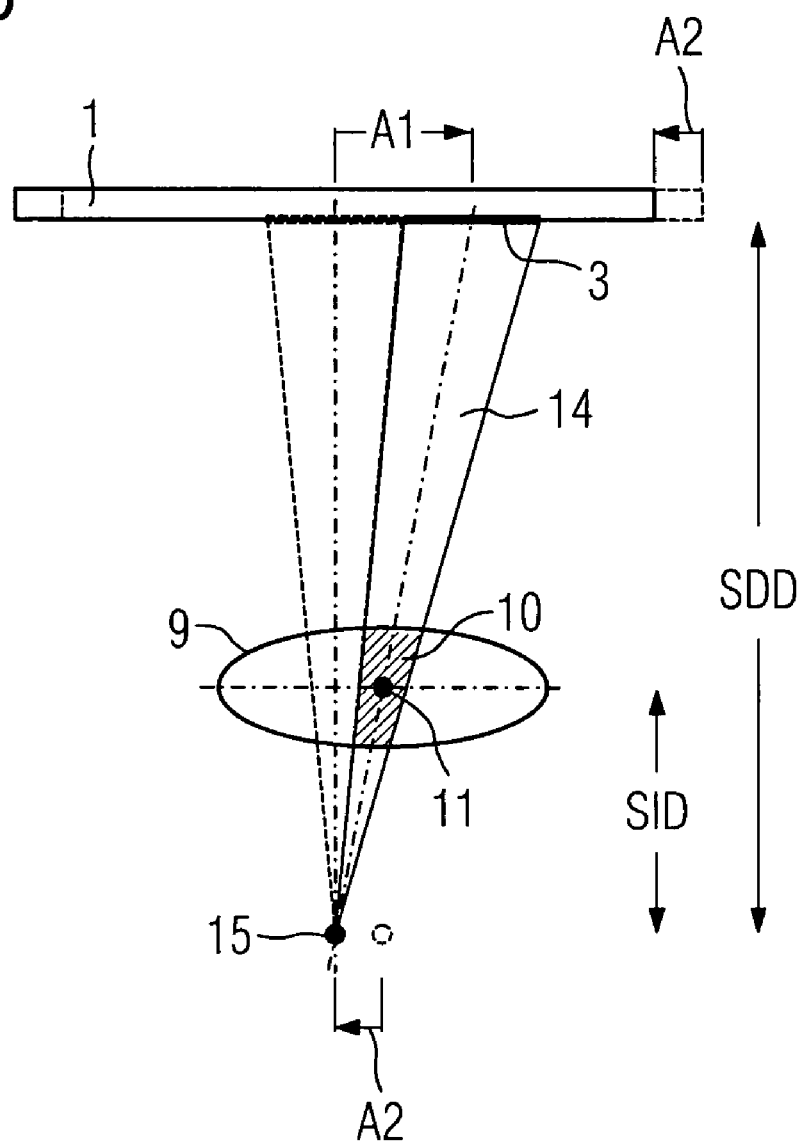
FIG. 6 shows a further illustration of the geometric ratios with an inventive method as claimed in FIG. 4.

FIG. 5 and FIG. 6 show the geometrical relationships with a method as claimed in FIG. 4 in different states, with FIG. 5 indicating the initial state with a solid line and the state after the movement of the recording system by the second distance A2 being illustrated by a dashed line and FIG. 6 indicating the state after the movement of the recording system with a dashed line and indicating the state after the movement of the measuring surface by the first distance A1 with a solid line.

Figure 7:
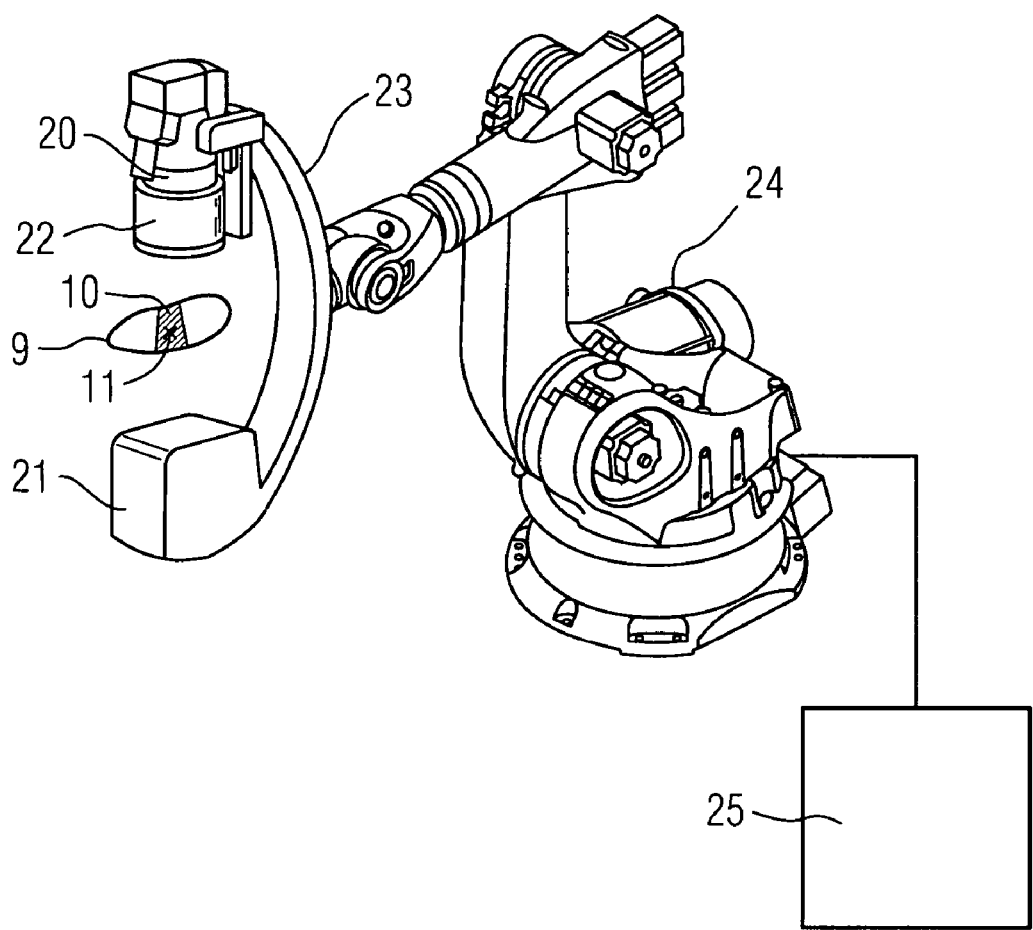
FIG. 7 shows an x-ray system according to the invention with a C-arm which can be moved by an industrial robot.

FIG. 7 shows an x-ray system according to one embodiment of the invention, which comprises an industrial robot 24 with six axis of rotation. A C-arm 23 is mounted on the industrial robot in a rotatable fashion, on one end of which is arranged an x-ray source 20 having a diaphragm system 22 and on the other end of which is arranged an x-ray detector 21. An object 9 with an examination area 10 is located between the x-ray source 20 and the x-ray detector 21, said object generally lying on an examination table. The object 9 is generally arranged such that the center point 11 of the examination area 10 coincides with the isocenter (=rotation center point of the recording system) of the C-arm 23. The diaphragm system 22 is used to form sub x-ray beams 13; 14 from the x-rays. The x-ray system comprises a control unit 25, which controls both the movements of the industrial robot 24, the rotations of the C-arm 23, the position of the diaphragm of the diaphragm system 22 and also generally the generation of x-rays and the recording of x-ray images by means of the x-ray detector 21.

In addition to an x-ray system with a bracket, on which the x-ray source and the x-ray detector can be mounted in a fixed manner and are herewith mechanically coupled in a fixed orientation and at a fixed distance, an x-ray system according to one embodiment of the invention can also merely comprise an electronic coupling between the x-ray source and x-ray detector, which provides that the x-ray source and x-ray detector are permanently at a fixed distance relative to one another. An x-ray system of this type can be built for instance from two industrial robots, with one industrial robot supporting the x-ray source and the other industrial robot supporting the x-ray detector. With such an x-ray system, the control facility is also designed such that it controls an electronic coupling between the x-ray source and the x-ray detector.

The invention can be summarized as follows: To avoid manual readjustments, provision is made for a method for displacing a superimposed measuring surface on a sensor surface of an x-ray detector with an x-ray system, comprising a x-ray source and the x-ray detector, with the x-ray source and the x-ray detector forming a recording system and comprising a fixed orientation and a fixed distance relative to one another, with the recording system being moveable in a three-dimensional manner relative to an object, having the following steps:

the superimposed measuring surface is moved on the sensor surface of the x-ray detector by a first distance in a first direction, and the recording system is moved by a second distance in parallel to the first distance in a second direction, which is opposite to the first direction, whereby after implementing one of the two steps, an adjustment of the respective second step is automatically carried out so that a previously superimposed examination area of the object remains superimposed on the displaced measuring surface.

The invention claimed is:

1. A method for displacing a superimposed measuring surface of a recording system having an x-ray source and an x-ray detector, comprising:
   displacing the superimposed measuring surface on a sensor surface of the x-ray detector by a first distance in a first direction; and
   automatically moving the recording system by a second distance parallel to the first distance in an opposite direction to the first direction so that an examination area of an object to be examined remains identically superimposed on the displaced superimposed measuring surface.

2. The method as claimed in claim 1, wherein the recording system is three-dimensionally moveable relative to the object.

3. The method as claimed in claim 1, wherein the recording system is mounted on a bracket that is rotatable about an isocenter between a focus of the x-ray source and the x-ray detector.

4. The method as claimed in claim 3, wherein the bracket is a C-arm and moved by an industrial robot.

5. The method as claimed in claim 1, wherein the superimposed measuring surface is displaced from a central position on the sensor surface into an eccentric position on the sensor surface.

6. The method as claimed in claim 1, wherein the superimposed measuring surface is displaced first by the first distance and then the recording system is subsequently moved by the second distance.

7. The method as claimed in claim 6, wherein the second distance is determined by parameters of: distance from a focus of the x-ray source to the x-ray detector, distance from a focus of the x-ray source to a center point of the examination area, and the first distance.

8. The method as claimed in claim 1, wherein the recording system is moved first by the second distance and the superimposed measuring surface is subsequently displaced by the first distance.

9. The method as claimed in claim 8, wherein the first distance is determined by parameters of: distance from a focus of the x-ray source to the x-ray detector, distance from a focus of the x-ray source to a center point of the examination area, and the second distance.

10. The method as claimed in claim 1, wherein the superimposed measuring surface is displaced by adjusting a diaphragm system in order to form a sub x-ray beam from x-rays emitted by the x-ray source.

11. The method as claimed in claim 1, wherein the examination area and the displacement of the measuring surface is determined or selected by an operator.

12. An x-ray system for recording an x-ray image of an examination area of an object, comprising:
    a recording system comprising an x-ray source that emits x-rays and an x-ray detector with a sensor surface that detects the emitted x-rays;
    a diaphragm system that forms a sub x-ray beam from the emitted x-rays that radiates a superimposed measuring surface on the sensor surface; and
    a control unit that controls:
        a displacement of the superimposed measuring surface by a first distance in a first direction, and
        a movement of the recording system by a second distance parallel to the first distance in an opposite direction of the first direction so that the examination area of the object remains identically superimposed on the displaced superimposed measuring surface.

13. The x-ray system as claimed in claim 12, wherein the diaphragm system is automatically controllable.

14. The x-ray system as claimed in claim 12, wherein the superimposed measuring surface is smaller than the sensor surface.

15. The x-ray system as claimed in claim 12, wherein the recording system is three-dimensionally moveable relative to the object.

16. The x-ray system as claimed in claim 12, wherein the superimposed measuring surface is displaced from a central position on the sensor surface into an eccentric position on the sensor surface.

17. The x-ray system as claimed in claim 12, wherein the superimposed measuring surface is displaced first by the first distance and then the recording system is subsequently moved by the second distance.

18. The x-ray system as claimed in claim 17, wherein the second distance is determined by parameters of: distance from a focus of the x-ray source to the x-ray detector, distance from the focus of the x-ray source to a center point of the examination area, and the first distance.

19. The x-ray system as claimed in claim 12, wherein the recording system is moved first by the second distance and the superimposed measuring surface is subsequently displaced by the first distance.

20. The x-ray system as claimed in claim 19, wherein the first distance is determined by parameters of: distance from the focus of the x-ray source to the x-ray detector, distance from the focus of the x-ray source to a center point of the examination area, and the second distance.

* * * * *